US007833700B2

(12) United States Patent
Malmsten et al.

(10) Patent No.: US 7,833,700 B2
(45) Date of Patent: Nov. 16, 2010

(54) METHOD OF CONCENTRATING AND RECOVERING A VIRAL ENZYME ACTIVITY FROM BIOLOGICAL SAMPLES

(75) Inventors: Anders Malmsten, Uppsala (SE); Ingvar Pettersson, Uppsala (SE); Tommy Gatu, Uppsala (SE); Clas Källander, Uppsala (SE); Simon Gronowitz, Uppsala (SE)

(73) Assignee: Cavidi AB, Uppsala (SE)

( * ) Notice: Subject to any disclaimer, the term of this patent is extended or adjusted under 35 U.S.C. 154(b) by 2166 days.

(21) Appl. No.: 10/239,172

(22) PCT Filed: Mar. 22, 2001

(86) PCT No.: PCT/SE01/00617

§ 371 (c)(1),
(2), (4) Date: Sep. 25, 2002

(87) PCT Pub. No.: WO01/75147

PCT Pub. Date: Oct. 11, 2001

(65) Prior Publication Data

US 2003/0104441 A1  Jun. 5, 2003

(30) Foreign Application Priority Data

Mar. 29, 2000  (SE) .................................. 0001132

(51) Int. Cl.
*C12Q 1/25* (2006.01)
*C12N 7/02* (2006.01)
*A61K 39/21* (2006.01)

(52) U.S. Cl. .................... 435/5; 424/207.1; 435/239

(58) Field of Classification Search .................... 435/5, 435/39, 183, 810
See application file for complete search history.

(56) References Cited

U.S. PATENT DOCUMENTS

| 4,707,439 | A | * | 11/1987 | Seto et al. | ...................... 435/5 |
| 5,482,834 | A | * | 1/1996 | Gillespie | ...................... 435/6 |
| 5,498,520 | A | * | 3/1996 | Chapman | ...................... 435/5 |
| 5,658,779 | A | | 8/1997 | Krupey et al. | |
| 5,661,023 | A | * | 8/1997 | Hrinda et al. | ................ 435/239 |

FOREIGN PATENT DOCUMENTS

EP  0186526 A1  2/1986

OTHER PUBLICATIONS

O'Neil, Virus Harvesting and Affinity Based Liquid Chromatography, Feb. 1993, Bio/Technology vol. 11, pp. 173-178.*

* cited by examiner

*Primary Examiner*—Stacy B Chen
(74) *Attorney, Agent, or Firm*—Bacon & Thomas, PLL

(57) ABSTRACT

A method of concentrating and recovering an enzyme activity from enveloped viruses present in a biological sample, is described. The method comprises contacting the biological sample in a first buffer solution with a virus-binding matrix, such as an anion exchanger matrix, to attach virus particles present in the sample to the matrix, washing the matrix carrying the virus particles with a second buffer solution to remove components interfering with viral enzyme activity, lysing the immobilized virus particles in a third buffer solution and recovering the concentrated viral enzyme activity from the third buffer solution. Additionally, a commercial package containing written and/or data carrier instructions for performing laboratory steps for concentration and recovery of an enzyme activity from enveloped viruses present in a biological sample and at least one component necessary for the assay, is disclosed.

13 Claims, 3 Drawing Sheets

Figure 1:
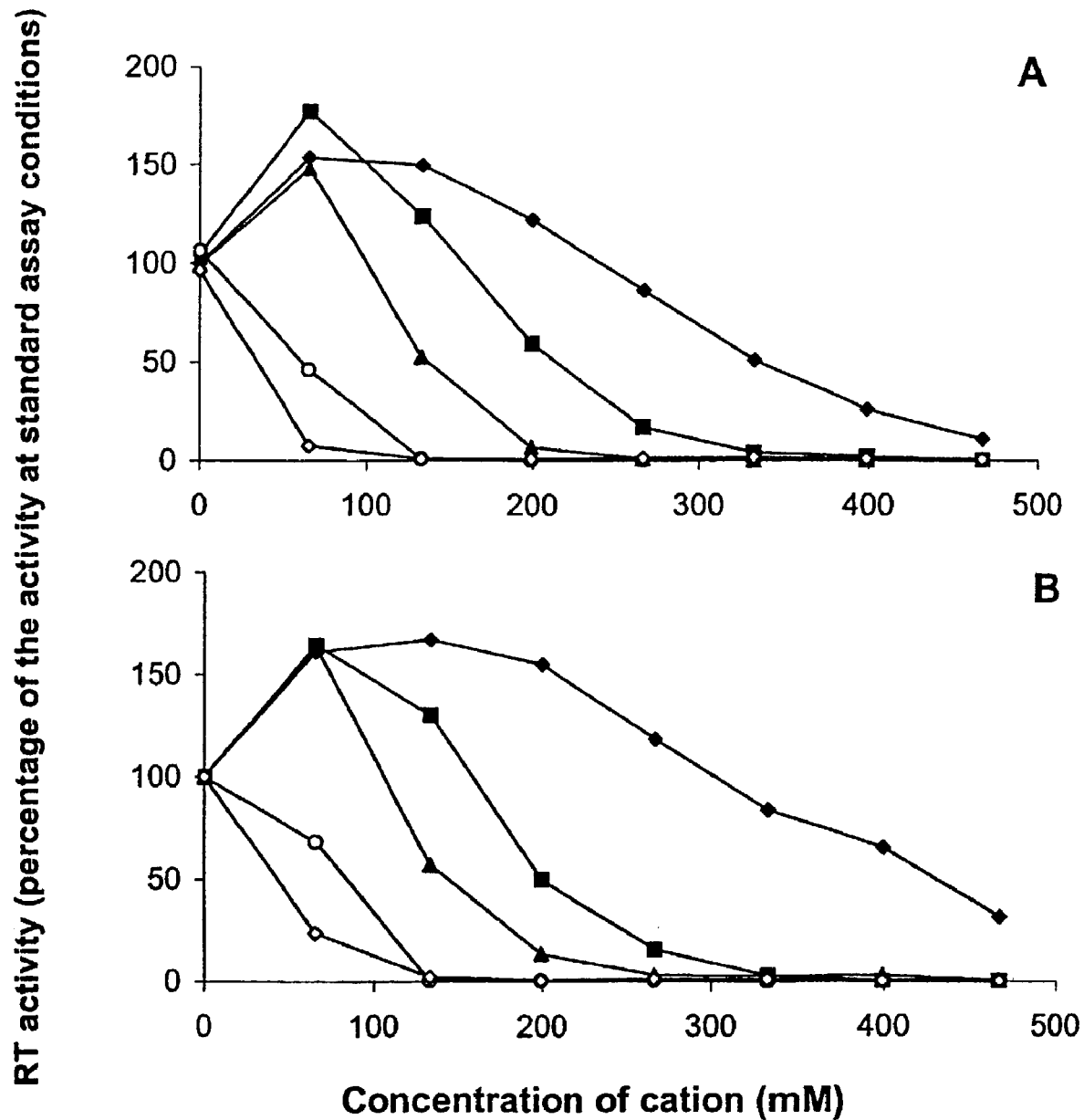

METHOD OF CONCENTRATING AND RECOVERING A VIRAL ENZYME ACTIVITY FROM BIOLOGICAL SAMPLES

This application is a national stage filing under 35 U.S.C. 371 of PCT/SE01/00617, filed Mar. 22, 2001.

The present invention relates to a method of concentrating and recovering a viral enzyme activity from biological samples. More precisely, the invention relates to a method of concentrating and recovering an enzyme activity from enveloped viruses present in a biological sample. The invention also relates to a commercial package useful in the performance of the method of the invention.

BACKGROUND OF THE INVENTION

In a virion (virus particle), the viral nucleic acid is covered by a protein capsid, and in some of the more complex animal viruses, the capsid itself is surrounded by an envelope containing membrane lipids and glycoproteins. Among these enveloped viruses, the ones receiving most attention today are the different retroviruses, especially HIV (Human immunodeficiency virus). The name retrovirus comes from the direction of the flow of genetic information for these viruses, from RNA to the DNA of the cell. Some retroviral strains are found to be symbiotic in one species and pathogenic in another. These findings indicate a potentially severe problem with xenotransplantation (transplantation of animal organs in humans). Both endogenous and exogenous retroviruses can contribute to vertical and horizontal transmission of genetic material within and between species and provide mechanisms for evolution of new pathogenic agents.

During the last decade there has been an increasing demand for methods for diagnosis and monitoring of retroviral infections as well as for research on the pathogenesis of new retroviruses. The state of the art is best illustrated by the methods currently used in the management of HIV infection. In the laboratory HIV-infection is detected and monitored by measurement of a) antibodies to HIV antigen, b) circulating HIV antigen, c) virus isolation, d) HIV RNA in circulation, and e) provirus DNA integrated in cells. The method of choice depends on the purpose of the test, and the stage of disease.

The currently accepted marker for viral load in the clinical setting is measurement of copy number of HIV RNA in plasma This can be accomplished either by PCR, NASBA, or by branched DNA techniques [Revets el al., 1996]. Currently used assays have a detection limit of 20 RNA copies/ml plasma [Perrin et al., 1998]. As all techniques for detection of viral nucleic acids are based on the binding of sequence specific primers, there is a significant risk that they will not hybridize to new strains or sequence variants in a sample.

Another important aspect concerning in vitro measurements of infection parameters emerges when extrapolating the results for the in vivo situation. Several of the laboratory techniques involve an amplification stage during which a selection step occurs. In the worst case the major viral variants amplified are those best matching the primers used, not the most abundant in the in vivo situation.

Direct measurement of viral enzymes in samples from the patient's blood would therefore be an attractive alternative to cell culture or the nucleic acid based methods both for quantification of viral replication and for studies of the effect of antiviral substances. The obstacles to overcome are both the assay sensitivity and to reproducibly separate the enzyme from host-specific enzymes and activity inhibiting substances.

The present invention enables measurement of an enzyme activity from an enveloped virus present in a biological sample by concentrating and recovering the enzyme activity without isolating the virions.

The prior art methods designed for concentration and purification of different viruses are either specific methods based on the antigenic properties of the virus proteins or generalized methods based on basic chemical or physical characteristics of the virus. Only the latter type of methods can be considered relevant for purification of antigenically highly variable retrovirus like HIV.

Viruses have traditionally been partly purified by different types of centrifugation, either by just pelleting the virus or in combination with the use of precipitating agents such as polyethylene glycol (U.S. Pat. No. 5,661,022). Centrifugation in density gradients results in more pure virus preparations (U.S. Pat. No. 4,729,955).

Another approach has been to bind the virus to different types of adsorbents. Porath and Jansson (U.S. Pat. No. 3,925,152) used insoluble organic macroporous polymers selected from the group consisting of agar, agarose, dextran and cellulose containing amphoteric substitutents composed of both basic nitrogen containing groups and carboxylate or sulphonated groups: Adsorbed viruses could in their system be eluted with solutions of successively different ionic strength to obtain virus variant separation. Their pioneering work has during the last two decades been followed in many related purification techniques based on interaction of viruses with gels with either anionic or cationic ionexchange residues (U.S. Pat. No. 3,655,509). Retroviruses and the related hepatitis B virus has for example been purified using both cation exchange (U.S. Pat. No. 5,447,859, U.S. Pat. No. 4,138,287) or anion exchange (U.S. Pat. No. 5,837,520, U.S. Pat. No. 5,661,023). The methods cited above are all based on binding the virus at low ionic strength and elution at high ionic strength.

Yet another approach for purification of virus and viral nucleic acid is based on binding virus to a water insoluble cross-linked polyhydroxy polycarboxylic acid polymer (U.S. Pat. No. 5,658,779). The virus is bound to the polymer at pH 6.0 to 8.0, probably by hydrophobic interactions and can be desorbed at pH 8.0 to 11.0. One interesting application of this technique concerns isolation of viral nucleic acid. In one such example bacteriophages from a bacterial lysate are in a first step adsorbed to the polymer. The polymer is then washed and the bound virus is disrupted using either a chelating agent, like EDTA, or a denaturating agent, like SDS. The viral proteins then adsorb to the polymer and a viral nucleic acid essentially free of interacting proteins is achieved. Use of a similar approach for purification of viral proteins is claimed but the technique described will release the viral proteins together with all other cellular and viral components adsorbed to the polymer.

The present inventors have conducted extensive research on measurements of the activity of the viral enzyme reverse transcriptase (RT). RT activity has previously been measured directly in serum or plasma [Awad, R. J. K. et al 1997, Ekstrand et al 1996]. One problem encountered in these early studies was the induction of high titers of RT activity inhibiting antibodies soon after primary infection. Another was the occasional occurrence of RT inhibitors in samples from HIV negative controls.

DESCRIPTION OF THE INVENTION

The present invention provides a solution to the above mentioned prior art problems. Further, it can be used for concentration of viral enzyme activity from large volumes of fluids i.e. cell culture supernatants containing very small virus amounts. Another application is to transfer viral enzyme from virions in highly inhibitory samples such as extracts from tissues or cultured cells into an environment that is compatible with enzyme assay conditions.

Thus, the current invention provides a method of concentrating and recovering viral enzyme activity, particularly from enveloped viruses, from crude biological samples such as blood, plasma, serum, cell culture fluid and cell extracts. It is based on a separation step in which the virions are captured on a solid matrix. Enzyme inhibitory antibodies and other inhibitory substances are removed by a wash step and the enzymes are released by lysing the immobilized virions. Both the binding and the lysis steps are critical. The binding step must have the capacity to almost quantitatively immobilize small amounts of virions from biological fluids containing very high protein concentrations, such as serum or plasma, preferentially without binding immunoglobulin (Ig) or other potentially inhibitory substances. The lysis step should nearly quantitatively release the viral enzymes into an environment which prevents the enzyme from binding to the separation matrix, stabilizes the native enzyme and is compatible with optimal assay conditions.

In particular, the present invention is directed to a method of concentrating and recovering an enzyme activity from enveloped viruses present in a biological sample comprising the steps of contacting the biological sample in a first buffer solution at a concentration in range of 100-500 mM of buffering substance and having a pH of 4.0-8.5 and optionally containing chaotropic ions at an ionic strength of up to 2 M with a virus-binding matrix, to attach virus particles present in the sample to the matrix, washing the matrix carrying the virus particles with a second buffer solution at a concentration of 1-100 mM of buffering substance and containing cations at a concentration of 0.1-1 M and having a pH of 4-9, to remove components interfering with viral enzyme activity, lysing the immobilized virus particles in a third buffer solution at a concentration of 10-500 mM of buffering substance and containing a non denaturing detergent and having a pH of 6-9, and recovering the concentrated viral enzyme activity from the third buffer solution.

In an embodiment of the invention the virus-binding matrix is an anion exchanger matrix, e.g. an anion exchanger matrix containing tertiary and/or quaternary amine groups, such as Fractogel® EMD DMAE and Fractogel® EMD TMAE equilibrated in 150 mM MES (2-(N-Morpholino)ethanesulfonic acid) pH 6.0.

In further embodiments the first buffer is selected from the group consisting of 150 mM MES pH 6.0, and 200 mM Potassium iodide (KI), the second buffer is selected from the group consisting of 10 mM MES pH 6.0, and 500 mM Potassium acetate (KAc), and the third buffer is selected from the group consisting of an enzyme assay compatible buffer including a detergent, e.g. 1% Triton X 100 and a buffering substance, e.g. 100 mM N-(2-Hydroxyethylpiperazine-N'-(2-ethanesulfonic acid) (Hepes) pH 7.6.

In a particularly preferred embodiment the concentrated and recovered viral enzyme activity is reverse transcriptase (RT) activity.

The biological sample is preferably selected from the group consisting of serum and plasma samples.

The present invention is also directed to a commercial package useful in the performance of the method of the invention. The package contains written and/or data carrier instructions for performing laboratory steps for concentration and recovery of an enzyme activity from enveloped viruses present in a biological sample, and at least one of the components a virus-binding matrix, a first buffer solution at a concentration in range of 100-500 mM of buffering substance and having a pH of 4.0-8.5 and containing chaotropic ions at an ionic strength of up to 2 M, a second buffer solution at a concentration of 1-100 mM of buffering substance and containing cations at a concentration of 0.1-1 M and having a pH of 4-9, a third buffer solution at a concentration of 10-500 mM of buffering substance and containing a non denaturing detergent and having a pH of 4-9, Mini columns, and Plastic tubes.

In a preferred embodiment of the commercial package the virus-binding matrix is an anion exchanger matrix, the first buffer is selected from the group consisting of 150 mM MES pH 6.0, and 200 mM Potassium iodide (KI), the second buffer is selected from the group consisting of 10 mM MES pH 6.0, and 500 mM Potassium acetate (KAc), and the third buffer is selected from the group consisting of a RT assay compatible buffer including a detergent, e.g. 1% Triton X 100 and a buffering substance, e.g. 100 mM (N-(2-Hydroxyethylpiperazine-N'-(2-ethanesulfonic acid) (Hepes) pH 7.6.

In a particularly preferred embodiment the anion exchanger matrix is an anion exchanger matrix containing tertiary and/or quaternary amine groups, such as Fractogel® EMD DMAE and Fractogel® EMD TMAE equilibrated in 150 mM MES (2-(N-Morpholino)-ethanesulfonic acid) pH 6.0.

Considerations Regarding Choice of Buffers

A) Binding Buffer (the First Buffer)

The binding buffer is used to adjust the pH and ionic strength in the sample to values giving maximal binding of the virus particles and at the same time minimizing binding of host components, such as plasma/serum proteins, and particularly antibodies as well as other potentially inhibitory substances.

1) pH

With an anion exchanger and FIV virus we found binding with buffers between pH 7.5 and 5.0 in a system without plasma components. With regard to the isoelectric point (Ip) of the plasma components which should not bind, a pH as low as possible should be used. Fresh EDTA plasma samples has a pH of approximately 8.5. Depending on handling (e.g. storage) the pH in such samples may drop to approximately 8.0.

A number of buffers were investigated with regard to the ability to normalize pH in different plasmas to a defined pH in the range 3.0-7.5.

Two problems were encountered with pH values below 6.0.
a) pH values below 5.0 were not possible to achieve with concentrations of buffer up to 0.5 M.
b) When using a 1:1 mixture of plasma and buffer, precipitates occurred at pH values below 6.0. Centrifugation experiments confirmed that virus particles in plasma also started to precipitate at pH below 6.0

Chosen values for the preferred pH range is therefore 4.0-8.5, and pH 6.0 is considered optimal.

The chosen concentration of buffer should be in the range of 100-500 mM, and 150 mM is considered optimal.

Two buffers functioning in the pH range of approximately 6.0 were investigated, namely (bis(2-Hydroxyethyl)iminotris (hydroxymethyl)methane; 2-bis(2-Hydroxyethyl)-amino-2 (hydroxymethyl)-1,3-propanediol) (Bis-Tris) and MES.

Bis-Tris is basic and requires pH adjustment with large amounts of acid. At different pH values a mixture of pH effect and ionic strength is therefore obtained MES is acidic and requires less adjustment to give the required pH. Binding experiments indicated that the MES buffer functions slightly better, and this buffer was selected for studies on the significance of the ionic strength.

II) Ionic Strength

As the pH range was decided upon, we investigated at which ionic strength and with which negative ions present the virus particles still bound. Sulfate, acetate, chloride and iodide were primarily used.

Two ions far apart in the chaothropic series, acetate (Ac) and iodide, were studied in a broader concentration range. The effects were the expected: The iodide started to affect the binding of virus at a lower concentration than acetate.

The binding was reduced with 50% by 500 mM of iodide, but 2 M of Ac is required for this effect.

The amount of bound Ig that could be eluted from the gel was investigated after binding and washing of FIV in plasma with different combinations of Ac and iodide in the buffers.

Having no salts present at the binding gave higher residual amounts of Ig after lysis (even though the gel had already been washed with salt). Iodide was more efficient than Ac, that gave approximately 1.5 times higher amount of residual Ig. By combining different salts in the two steps it was shown that iodide in the binding but Ac in the wash was equally efficient as iodide throughout.

Useful negative ions may be weak eluents like Ac to strong eluents as iodide as well as those ions found between these with regard to properties in the chaothropic series, preferably Ac, Cl and iodide, and particularly iodide.

Chosen values for the ionic strength may be varied and may be up to 2 M, preferably 0.1-1 M, and particularly 200 mM for iodide and 1 M for Ac, respectively.

B) Wash Buffer (the Second Buffer)

1) The buffer shall, as effectively as possible, remove factors which may interfere with the measurement/recovery of viral enzymes from the gel. It is particularly important to remove antibodies.

2) The buffer must not remove virions from the gel or lyse virions.

3) Since the components of the buffer, after a certain dilution (approx. 5-9 times), will be present in the enzyme assay, the components may not severely inhibit the enzyme.

Critical factors for the wash buffer are the pH and the ionic strength.

I) pH

Proteins bind and remain bound to an anion exchanger at pH above their isoelectric point. The Ip of different immunoglobulins varies, but lies on the average at pH 8.9.

Our experiments with FIV virions showed that virus in a buffer containing 0.1 M KCl did bind very well to several different anion exchangers in the pH range of 5.8-7.6. The recovery at lysis after washing with buffer at the same pH was high throughout the whole pH range. Ip for FIV is thus<5.8.

The chosen pH range for the wash buffer is pH 4-9 (even though possibly lower pH values may be possible to use).

Preferably the pH range is 5.5-8 (the washing effect on Ig is likely to be poor above 8.0), and especially 6-7.5. The buffer substance should be present at a relatively low concentration which is sufficient to keep the pH stable, but which does not require a too high concentration of buffer substance to change the pH at the lysis stage.

Chosen range for the concentration of buffer substance is 1-100 mM. Preferably 5-50 mM and optimally 10 mM.

II) Ionic Strength

Too high concentrations of cation may release virus at wash, too low concentrations give residual Ig and other inhibiting substances in the lysate.

The concentration limits are influenced by the actually used caeothropic cation. The principal is to use as high a concentration as possible which does not release the virus.

The concentration is also limited by the effect of the ion in the enzyme (e.g. RT) assay after dilution (approx. 5-9 times), see Example 4.

Different anionic exchangers probably give more or less residual Ig, depending on the properties of the matrix, at a given concentration of salt.

For example, the following applies when Fractogel TMAE is washed at pH 6.0.

1) Wash with Ac up to 0.5 M no loss of virus. At 1 M recovery of approx. 50%. Up to 0.25 M still approx. 0.2% residual Ig. At 0.5 M and higher<0.02% residual Ig.

2) Wash with chloride ($Cl^-$) up to 0.25 M no loss of virus, at 0.5 M approx. 50%, at 1 M all the virus is lost. Residual Ig at $Cl^-$ of 0.25 M and higher<0.02%.

3) High concentration of iodine in the absence of serum protein seems to irreversibly affect the virus so that we could not recover any enzyme (RT) activity. Iodine is therefore good at the binding stage but should not be used in the wash buffer.

Chosen range for the concentration of cation in wash buffer is 0.1-1 M, preferably 0.2-0.6 M, and particularly $Ac^-$ or $Cl^-$ is used at 0.2-0.6 M.

C) Lysis Buffer (the Third Buffer)

The lysis step should nearly quantitatively release the viral enzymes into an environment which prevents the enzyme from binding to the separation matrix, stabilizes the native enzyme and is compatible with optimal assay conditions.

I) Detergent

Detergent is necessary for the lysis of the virus. There are a vast number of detergents, and in the present context the detergent should be a "non denaturating detergent" e.g. Polyoxyethanesorbitan (Tween) or t-Octylphenoxypolyethoxyethanol (Triton X-100) Different detergents are more or less effective for lysis of virions and their interference in the enzyme (RT) assay at high concentrations is rather minimal. Therefore no specific range for the concentration is necessary. It may be mentioned that Triton X 100 is not effective at 0.1% and starts to induce problems at 5%.

II) pH

The pH must be compatible with the pH of the chosen enzyme assay. Furthermore, the pH shall not allow binding of viral enzyme to the ion exchanger. We have found that there is no binding of FIV or HIV RT at pH 5.5-8.5, and that Ip for HIV RT lies in the vicinity of 9.1. The effect of pH on enzyme assay is therefore of major importance.

Chosen pH range is 4-9, preferably 7-8, and optimally 7.6.

The buffering substance shall be added at a sufficiently high concentration to adjust the pH from 6.0 to 7.6. The required concentration varies of course with the concentration in the wash buffer. Too high a concentration may interfere in the enzyme assay. Chosen range of the concentration of buffering substance is 10-500 mM, preferably 50-200 mM, and optimally 100 mM.

Of course the buffer solution may contain additional components favorable for the chosen enzyme assay.

The invention will now be illustrated by the following description of embodiments, particularly procedures adapted to provide RT samples, which can be accurately analyzed with regard to RT activity by our (Cavidi Tech) commercial colorimetric RT assays, e.g. described in our Swedish patent application 9902410-1. These embodiments and examples are not intended to limit the scope of the claimed invention.

General Description of the Performance of the Method of the Invention

Two slightly different embodiments of the invention are described.

I) Protocol for Batch Separation of Plasma.
1) Label the desired number of 15 ml plastic centrifuge tubes to identify the samples to be analyzed.
2) Suspend the separation gel carefully into a 1:1 gel slurry, and transfer 400 µl gel slurry to each labeled centrifuge tube. Spin down the gel and remove the buffer.
3) Mix 500 µl of each plasma to be analysed with an equal volume of the binding buffer (A).

Transfer each plasma-buffer mixture to the corresponding labeled centrifuge tube with gel. Add stopper, shake the tubes to suspend the gel into the sample and incubate for one hour on an orbital shaker at room temperature.
4) Prepare the wash buffer (B), 30 ml buffer/sample is needed
5) Allow the gel to settle and remove the supernatant. Add 10 ml wash buffer (B). Put the stopper back, resuspend the gel into the wash buffer by shaking. Let the gel sediment for approximately 10 minutes. Remove stopper, aspirate the wash fluid carefully to avoid aspirating gel.
6) Repeat the wash according to 6.
7) Repeat the wash according to 6.
8) Centrifuge the tubes at approximately 500 g for 5-10 minutes. Aspirate all wash buffer (B) above gel surface.
9) Add 180 µl lysis buffer (C) to each tube, add stopper and incubate for 30 min on an orbital shaker at room temperature.
10) Centrifuge the tubes at approximately 500 g for 5-10 minutes.

The RT activity recovered in the supernatant from step 10 can be quantitated with a sensitive RT activity assay, e.g. the Cavidi®HS-kits, which are based on the method described by Ekstrand et al 1996.

II) Protocol for Plasma Separation on Mini Columns
1) Label the desired amount of 15 ml plastic mini columns to identify the samples to be analyzed.
2) Prepare the wash buffer (B), 20 ml buffer/sample is needed
3) Suspend the separation gel carefully into a 1:1 gel slurry and transfer 1000 µl gel slurry to each column.
4) The plasma to be analyzed is diluted 1:1 in binding buffer (A). The system is optimized for the analysis of 500 µl plasma.
5) Open the column at both ends and let the buffer in each column run through. Add gently a maximum of 1000 µl sample according to 4) on top of each column. Close the column before it run dry and let the sample adsorb for 60 min before starting the wash procedure.
6) Each column is washed with 2×10 ml wash buffer (B).
7) When all wash buffer had passed through the columns add 200 µl lysis buffer (C) to each column, let the column run dry and incubate for 30 min at room temperature.
8) Move the columns to a rack with sample collection tubes and add another 300 µl lysis buffer (C) to each column. Collect the eluates which contain the RT from the virions present in the original samples.

The RT activity recovered in the the eluates from step 8 can be quantitated with a sensitive RT activity assay, e.g. the Cavidi® HS-kits, which are based on the method described by Ekstrand et al 1996.

Materials Used in a Preferred Embodiment

Separation gel: e.g. Fractogel® EMD TMAE, or Fractogel® EMD DMAE equilibrated in 150 mM MES (2-(N-Morpholino)ethanesulfonic acid) pH 6.0. Mini columns e.g. Biorad Poly-Prep® (7311553)

Plastic tubes

A) Binding buffer: 300 mM MES pH 6.0, 400 mM Potassium iodide (KI)

B) Wash buffer: 10 mM MES pH 6.0, 500 mM Potassium acetate (KAc)

C) Lysis buffer: A RT assay compatible buffer including a detergent e.g. 1% Triton X-100 and a buffering substance e.g. 100 mM (N-(2-Hydroxyethylpiperazine-N'-(2-ethanesulfonic acid) (Hepes) pH 7.6.

SHORT DESCRIPTION OF THE DRAWINGS

FIG. 1 shows two diagrams A and B, which show the effects of addition of different cations to the RT reaction mixture at standard assay conditions.

Symbols: Ac$^-$ (♦), Cl$^-$ (■), Br$^-$ (▲), I$^-$ (○), SCN$^-$ (◇).

Figure 2:
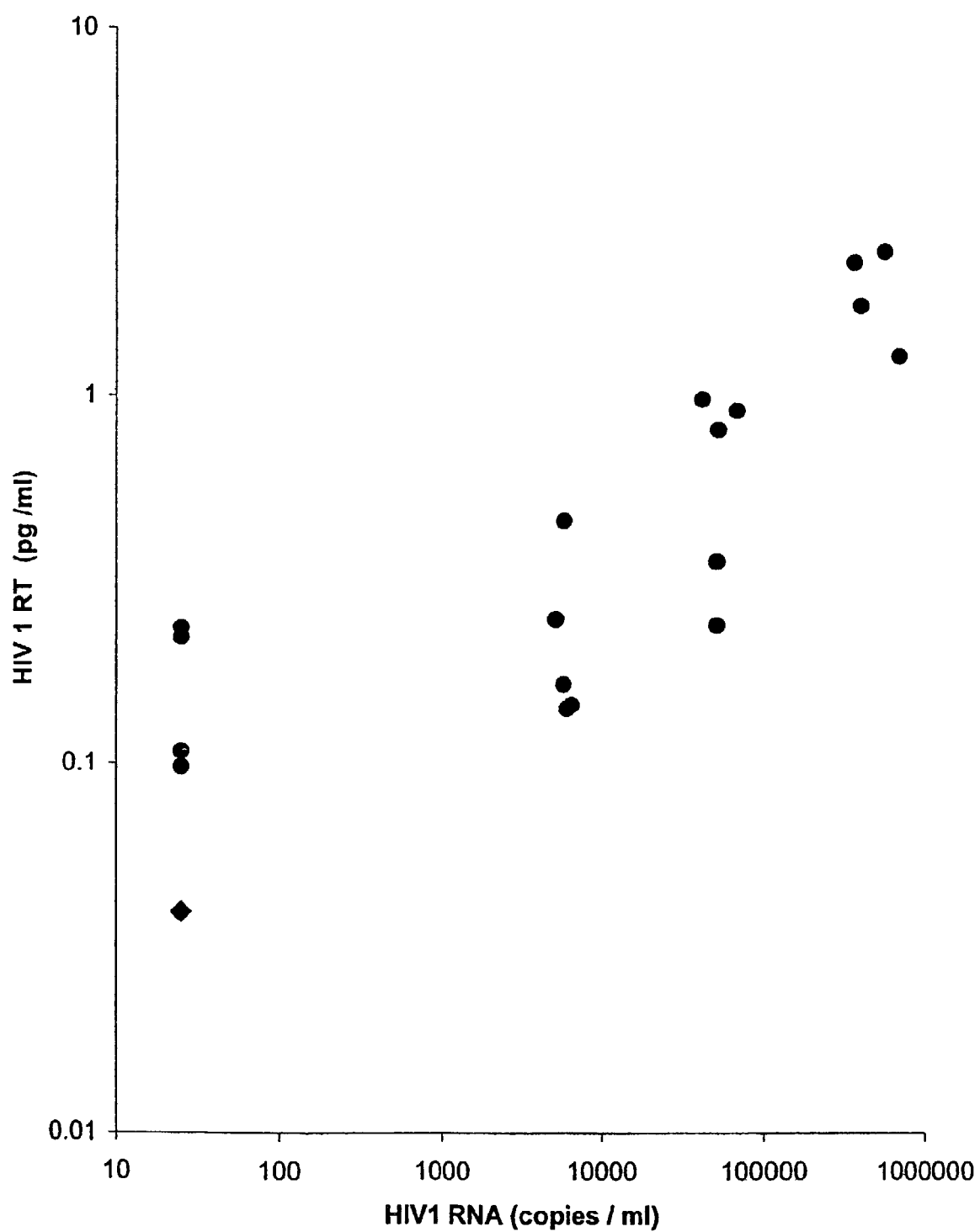

FIG. 2 is a diagram which shows the relation between amount of HIV RT recovered according to the invention and amount of viral RNA measured with HIV 1 RNA PCR.

Symbols: pooled plasma from 100 healthy blood donors ♦, plasma from HIV infected individuals ●

Figure 3:
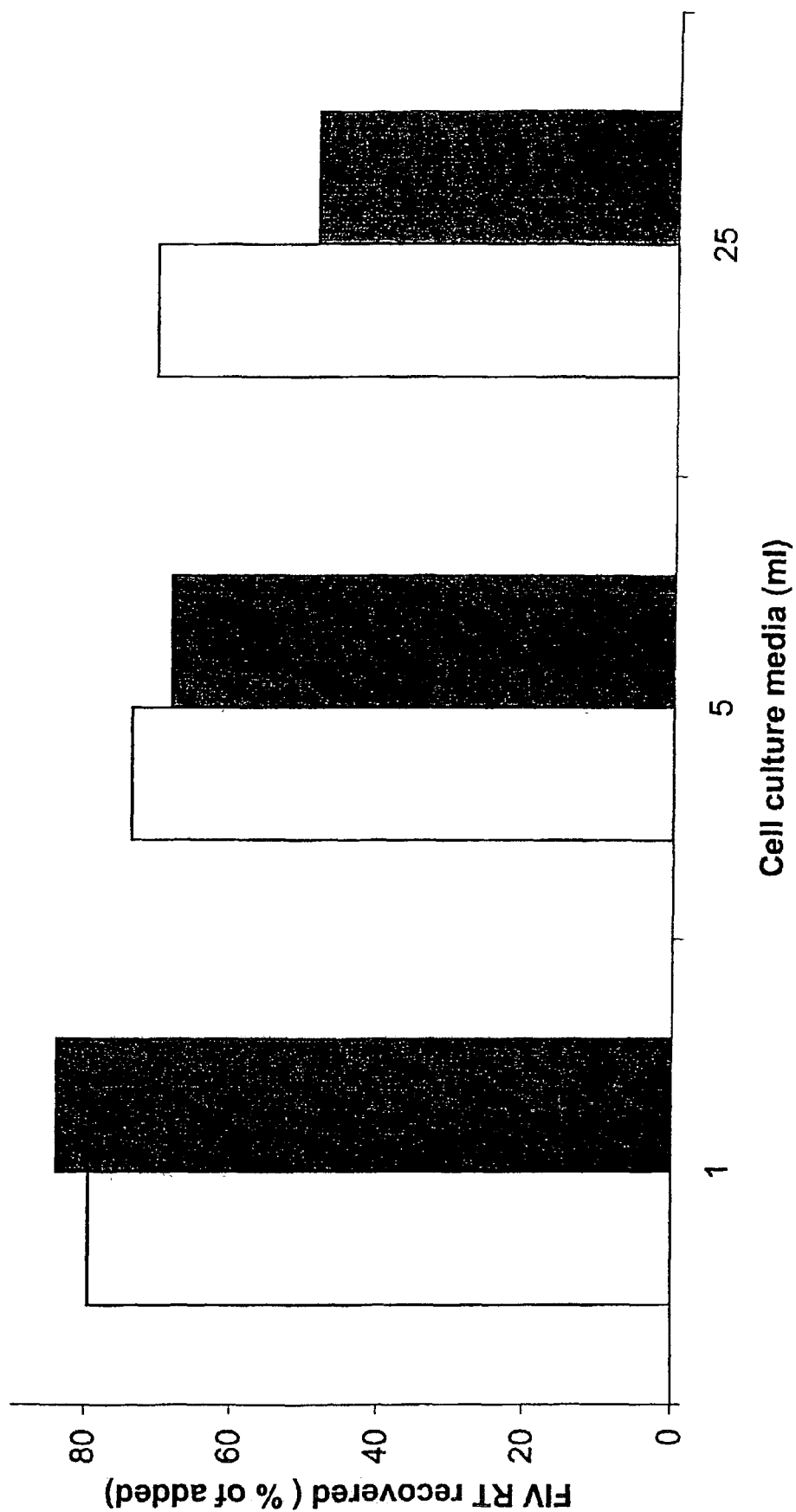

FIG. 3 is a diagram which shows detection of minute amounts of retrovirus by concentrating the RT activity from a large volume of cell culture media Symbols: 1% serum (open bar), 10% serum (closed bar).

EXAMPLES

Example 1

Screening of the capacity of various chromatography media to immobilize retrovirus (Table 1). 500 µl of a FIV spiked human plasma diluted 1:1 in binding buffer was mixed with 100 µl of indicated gel. After one hour 450 µl supernatant was withdrawn from each sample and replaced with 450 µl lysis buffer. The samples were then incubated for another 30 minutes and the amount of RT activity in each supernatant and lysis fraction was determined and calculated as a percentage of the RT activity added to the original sample. There was a considerable variation in virus binding capacity among the media tested. The highest binding capacity was found among anionic ion exchange media with tertiary or quaternary amines. The recovery of RT enzyme in the lysis fraction using the media with good binding capacity ranged from 53 to 100%, which indicated that no binding to the anionic exchanger of the released RT occurred during virus lysis. Our main criteria for selection of separation media was good virus binding capacity and high recovery of FIV RT.

Example 2

Recovery of RT activity from different retroviruses added to human plasma (Table 2). Four samples of a human plasma were spiked with one each of four different retroviruses. The samples were diluted 1:1 in sample dilution buffer and processed according to "Protocol for plasma separation on mini columns" using 500 µl of Fractogel TMAE highcap gel. Each RT was recovered in 300 µl lysis buffer and the amount of RT and Ig in the lysates were determined and recalculated as a percentage of the corresponding amounts in the original sample. Between 39 and 74% of the RT activity present in the original virus preparations were recovered in the 300 µl lysate fraction. The reduction in Ig concentration was between 2000 and 12000 times for the different samples.

Example 3

Effects of addition of different cations to the RT reaction mixture (FIG. 1). Chaotropic cations giving the indicated final concentrations were added to Cavidi HS kit Lenti RT reaction solutions. The effect of five different cations on the activity of two RTs was evaluated: A) FIV virions corresponding to 0.4 µU RT activity, B) Recombinant HIV 1 RT corresponding to 0.6 µU RT activity. The RT activity at each cation concentration was recalculated into percent of a control measured at standard conditions. The inhibitory effect of different cations was related to the chaotropic effect of the ions. The most chaotropic cations, $SCN^-$ and $I^-$ were inhibitory at all concentrations tested. Intermediate ions, $Br^-$ and $Cl^-$ stimulated the retroviral RTs at concentrations below 100 mM but were increasingly inhibitory at higher concentrations. From FIG. 1 it can be concluded that $Cl^-$ or $Br^-$ ions at concentrations up to 70 mM and $Ac^-$ ions up to 200 mM can be included in the reaction mixture without causing adverse effects.

Example 4

Relation between amount of HIV RT recovered according to the invention and amount of viral RNA measured with HIV 1 RNA PCR (FIG. 2). 200 µl samples of EDTA plasma from HIV infected individuals, and from a pool obtained from 100 healthy blood donors, were processed according to "Protocol for batch separation of plasma". The amount of RT activity recovered from each sample was determined in an overnight RT assay using Cavidi HS kit Lenti RT. The RT activities obtained were recalculated into pg HIV 1 RT according to an internal standard curve. The amount of HIV 1 RNA in each sample was measured by standard HIV 1 RNA PCR (Roche, Cobas Amplicor HIV monitor version 1.5). Values<50 RNA copies/ml have been plotted equal to 25 (FIG. 2). A strong correlation was found between amount of plasma RT recovered according to the invention and amount of HIV RNA measured with PCR (r=0.85, p<0.001, Spearman correlation by ranks).

Example 5

Detection of Minute Amounts of Retrovirus by Concentrating the RT Activity from a Large Volume of Cell Culture Media (FIG. 3)

Eagles minimum essential medium (MEM) containing either 1% (open bar) or 10% (filled bar) newborn calf serum (Gibco) was prepared. A small amount of FIV virions corresponding to 0.6 mU RT activity was added to 1, 5 and 25 ml samples from each MEM/serum mixture. Each sample was passed through a 1 ml DEAE A25 Sephadex mini column, followed by a wash with 20 ml wash buffer. Finally the RT activity was eluted into 300 µl elution buffer according to "protocol for plasma separation on mini columns". With this procedure we recovered more than 70% of the virus associated RT from 25 ml media as long as the serum concentration did not exceed 1%. The corresponding figure at 10% serum was approximately 50% (FIG. 3).

REFERENCES

Andersson L-O, Einarsson G. M., Kaplan L. P. Purifying and isolating method for hepatitis virus to use in preparing vaccine U.S. Pat. No. 4,138,287.

Awad, R. J. K., Corrigan, G. E., Ekstrand, D. H. L., Thorstensson, R., Källander, C. F. R. and Gronowitz, J. S. Measurement of levels of HIV-1 reverse transcriptase (RT) and RT activity blocking antibody human serum by a new standardised colorimetric assay. 1997 J. Clin. Microbiol. 35, 1080-1089.

Ekstrand, D. H., Bottiger, D., Andersson, H., Gronowitz, J. S. and Källander, C. F. R. Reverse transcriptase and corresponding activity blocking antibody in monitoring $SIV_{sm}$ infection in macaques. 1997 AIDS Res. Hum. Retroviruses 13, 601-610.

Ekstrand D. H., Awad R. J., Källander C. F., Gronowitz J. S. A sensitive assay for the quantification of reverse transcriptase activity based on the use of carrier-bound template and non-radioactive-product detection, with special reference to human-immunodeficiency-virus isolation. 1996, Biotechnol Appl Biochem, 23, 95-105.

Fields J., Johnson J. Process for the separation of virus from non-viral proteins. U.S. Pat. No. 3,655,509:

Hrinda M. E., Prior C. P., Mitschelen J. J., Irish T. W., Weber D. M., Gore R. S., Harter J. J. Bay P. M., Tarr G. C. Production and purification of retroviral particles using tentacle anion exchange U.S. Pat. No. 5,661,023:

Källander C., Petterson I, Gronowitz S. Reverse transcriptase assay kit, use thereof and method for analysis of RT activity in biological samples. Swedish patent application 9902410-1.

Kodama M., Sekiguchi K., Kubo M. Method of producing reverse transcriptase. U.S. Pat. No. 4,729,955:

Kotani H., Newton P., Zhang S. Purification of retroviral vectors. U.S. Pat. No. 5,661,022

Krupey J., Smith A. D., Arnold E., Donnelly R. Method of adsorbing viruses from fluid compositions. U.S. Pat. No. 5,658,779:

Perrin L., Yerly S., Marchal F., Schockmel G. A., Hirschel B., Fox C. H., Pantaleo G. Virus burden in lymph nodes and blood of subjects with primary human immunodeficiency virustype 1 infection on bitherapy. J Infect Dis 1998; 177 (6):1497-501

Porath J. O., Janson J-C. Virus separation. U.S. Pat. No. 3,925,152

Prussak C. Method for the purification or removal of retroviruses using sulfated cellulose U.S. Pat. No. 5,447,859

Revets H., Marissens D., de Wit S., Lacor P., Clumeck N., Lauwers S., Zissis G. Comparative evaluation of NASBA HIV-1 RNA QT, AMPLICOR-HIV monitor, and QUANTIPLEX HIV RNA assay, three methods for quantification of human immunodeficiency virus type 1 RNA in plasma. J Clin Microbiol 1996; 34(5):1058-64

Shabram P. W., Huyghe B. G., Liu X., Shepard H. M. Method of purification of viral vectors. U.S. Pat. No. 5,837,520:

substance and having a pH of 4.0-8.5 and optionally containing chaothropic ions at an ionic strength of up to 2 M with a virus-binding matrix, to attach virus particles present in the sample to the matrix, washing the matrix carrying the virus particles with a second buffer solution at a concentration of 1-100 mM of buffering substance and containing cations at a concentration of 0.1-1 M and having a pH of 4-9, to remove components interfering with viral enzyme activity, lysing the immobilized virus particles in a third buffer solution at a concentration of 10-500 mM of buffering substance and containing a non denaturing detergent and having a pH of 4-9 which prevents the enzyme from binding to the virus-binding matrix, and

TABLE 1

Screening of the capacity of various chromatography media to immobilize retrovirus.

| Trade Name | Type of interaction | Active group | Matrix | *RT activity in supernatant (%) | *RT activity recovered from gel (%) | *Total RT activity recovered (%) |
|---|---|---|---|---|---|---|
| Fraktogel, DEAE | anionic, weak | $R-CH_2N(C_2H_5)_2$ | methacrylate | 6 | 68 | 74 |
| DEAE-Si500 | anionic, weak | $R-CH_2N(C_2H_5)_2$ | silica | 9 | 96 | 105 |
| Fraktogel, DMAE | anionic, weak | $R-CH_2N(CH_3)_2$ | methacrylate | 9 | 73 | 83 |
| Fraktogel, TMAE | anionic, strong | $R-CH_2N + (CH_3)_3$ | methacrylate | 11 | 73 | 85 |
| Fraktogel, TMAE high cap | anionic, strong | $R-CH_2N + (CH_3)_3$ | methacrylate | 12 | 100 | 112 |
| DEAE Ceramics Hyper DF | anionic, weak | $R-CH_2N(C_2H_5)_2$ | ceramics | 19 | 98 | 117 |
| Macro prep High Q | anionic, strong | $R-CH_2N + (CH_3)_3$ | methacrylate | 21 | 72 | 93 |
| Macro prep DEAE support | anionic, weak | $R-CH_2N(C_2H_5)_2$ | methacrylate | 38 | 47 | 85 |
| Toyopearl DEAE 650M | anionic, weak | $R-CH_2N(C_2H_5)_2$ | methacrylate | 40 | 64 | 104 |
| AG4 - X4 | anionic, weak | $R-CH_2N(CH_3)_2$ | acrylic polymer | 40 | 64 | 104 |
| QAE sephadex A25 | anionic, strong | $R-CH_2N + (C_2H_3OHCH_3)(C_2H_5)_2$ | agarose | 42 | 53 | 96 |
| DEAE Sephadex A25 | anionic, weak | $R-CH_2N(C_2H_5)_2$ | dextran | 46 | 56 | 102 |
| Express ion exchange | anionic, weak | $R-CH_2N(C_2H_5)_2$ | cellulose | 50 | 57 | 107 |
| Sephadex G25 | control | none | dextran | 81 | 38 | 118 |

*percent of the RT activity added to the original sample.

TABLE 2

Recovery of RT activity from different retroviruses added to human plasma.

| Virus | RT added to plasma sample (mU RT activity) | RT Recovery (%) | Ig recovery (%) |
|---|---|---|---|
| FIV[a] | 0.24 | 66 | 0.023 |
| BLV[b] | 0.68 | 41 | 0.014 |
| JSRV[c] | 0.10 | 74 | 0.047 |
| MuLV[d] | 0.35 | 39 | 0.007 |

[a]Feline immunodeficiency virus
[b]Bovine leukemia virus
[c]Jaagsiekte sheep retrovirus
[d]Murine leukemia virus

The invention claimed is:

1. Method of concentrating and recovering a reverse transcriptase (RT) enzyme activity from enveloped retroviruses present in a biological sample
comprising the steps of
contacting the biological sample in a first buffer solution at a concentration in range of 100-500 mM of buffering recovering the concentrated viral enzyme activity from the third buffer solution.

2. Method according to claim 1, wherein the virus-binding matrix is an anion exchanger matrix.

3. Method according to claim 2, wherein the anion exchanger matrix contains tertiary and/or quaternary amine groups.

4. Method according to claim 1, wherein the first buffer is selected from the group consisting of 150 mM MES pH 6.0, 200 mM Potassium iodide (KI).

5. Method according to claim 1, wherein the second buffer is selected from the group consisting of 10 mM MES pH 6.0, 500 mM Potassium acetate (KAc).

6. Method according to claim 1, wherein the third buffer is selected from the group consisting of enzyme assay compatible buffers including a detergent and a buffering substance.

7. Method according to claim 1, wherein the biological sample is selected from the group consisting of serum and plasma samples.

8. Commercial package containing written and/or data carrier instructions for performing laboratory steps for concentration and recovery of a reverse transcriptase enzyme activity from enveloped retroviruses present in a biological sample, and the components a virus-binding matrix, a first buffer solution at a concentration in range of 100-500 mM of buffering substance and having a pH of 4.0-8.5 and containing chaothropic ions at an ionic strength of up to 2 M, a second buffer solution at a concentration of 1-100 mM of buffering substance and containing cations at a concentration of 0.1-1 M and having a pH of 4-9, a third buffer solution at a concentration of 10-500 mM of buffering substance and containing a non denaturing detergent and having a pH of 4-9, and optionally Mini columns, and Plastic tubes.

9. Commercial package according to claim 8, wherein the virus-binding matrix is an anion exchanger matrix, the first buffer is selected from the group consisting of 150 mM MES pH 6.0, 200 mM Potassium iodide (KI), the second buffer is selected from the group consisting of 10 mM MES pH 6.0, 500 mM Potassium acetate (KAc), the third buffer is selected from the group consisting of enzyme assay compatible buffers including a detergent and a buffering substance.

10. Commercial package according to claim 9, wherein the anion exchanger matrix contains tertiary and/or quaternary amine groups.

11. Method according to claim 2, wherein the first buffer is selected therefor the group consisting of 150 mM MES pH 6.0, 200 mM Potassium iodide (KI); the second buffer is selected from the group consisting of 10 mM MES pH 6.0, 500 mM Potassium acetate (KAc); and wherein the third buffer is selected from the group consisting of enzyme assay compatible buffers including a detergent and a buffering substance.

12. Method according to claim 11, wherein the biological sample is selected from the group consisting of serum and plasma samples.

13. Method according to claim 12 wherein the RT activity is quantitated with a sensitive assay.

* * * * *